US006288150B1

(12) United States Patent
Bier

(10) Patent No.: US 6,288,150 B1
(45) Date of Patent: Sep. 11, 2001

(54) UV-STABILIZERS FOR SILOXANE SYSTEMS

(75) Inventor: Peter Bier, Krefeld (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/445,233

(22) PCT Filed: May 28, 1998

(86) PCT No.: PCT/EP98/03156

§ 371 Date: Dec. 2, 1999

§ 102(e) Date: Dec. 2, 1999

(87) PCT Pub. No.: WO98/56852

PCT Pub. Date: Dec. 17, 1998

(30) Foreign Application Priority Data

Jun. 10, 1997 (DE) .............................................. 197 24 396

(51) Int. Cl.⁷ .................................................. C08K 5/3495
(52) U.S. Cl. ............................ 524/91; 524/588; 524/404; 524/413; 524/437; 427/387; 428/447; 528/28
(58) Field of Search ............................ 524/91, 261, 266, 524/404, 413, 437, 588; 528/28; 427/387; 428/447

(56) References Cited

U.S. PATENT DOCUMENTS

| 2,946,701 | 7/1960 | Plueddemann ............... 117/72 |
| 3,790,527 | 2/1974 | Merrill ............... 260/46.5 R |
| 3,865,755 | 2/1975 | Lannert ............... 252/558 |
| 3,887,514 | 6/1975 | Merrill ............... 260/33.6 SB |
| 4,006,271 | 2/1977 | French et al. ............... 427/164 |
| 4,051,161 | 9/1977 | Proskow ............... 260/448.8 R |
| 4,243,720 | 1/1981 | Schroeter et al. ............... 428/412 |
| 4,277,287 | 7/1981 | Frye ............... 106/287.12 |
| 4,278,804 | 7/1981 | Ashby et al. ............... 556/436 |
| 4,294,950 | 10/1981 | Kato ............... 528/14 |
| 4,315,091 | 2/1982 | Steinberger et al. ............... 528/28 |
| 4,324,712 | 4/1982 | Vaughn, Jr. ............... 524/767 |
| 4,368,235 | 1/1983 | Vaughn, Jr. ............... 428/412 |
| 4,455,403 | 6/1984 | Liebler ............... 524/300 |
| 4,456,647 | 6/1984 | Schonfelder et al. ............... 428/216 |
| 4,476,281 | 10/1984 | Vaughn, Jr. ............... 524/767 |
| 4,495,322 | 1/1985 | Liebler ............... 524/198 |
| 4,680,232 | 7/1987 | Factor et al. ............... 428/412 |
| 4,746,366 | 5/1988 | Philipp et al. ............... 106/287.19 |
| 5,438,142 | * 8/1995 | Fritsch et al. . |
| 5,556,936 | * 9/1996 | King, Jr. et al. . |
| 5,580,614 | 12/1996 | Amberg-Schwab et al. ............... 427/493 |
| 5,627,227 | * 5/1997 | Suga et al. . |
| 6,008,285 | 12/1999 | Kasemann et al. ............... 524/430 |

FOREIGN PATENT DOCUMENTS

| 37 06 714 | 9/1988 | (DE) . |
| 38 36 815 | 7/1990 | (DE) . |
| 39 17 535 | 12/1990 | (DE) . |
| 40 11 045 | 10/1991 | (DE) . |
| 40 20 316 | 1/1992 | (DE) . |
| 2001870 | 2/1979 | (GB) . |
| 2047721 | 12/1980 | (GB) . |
| 2048291 | 12/1980 | (GB) . |
| 05-287241 | * 2/1993 | (JP) . |

* cited by examiner

Primary Examiner—Robert Dawson
Assistant Examiner—Marc S. Zimmer
(74) Attorney, Agent, or Firm—Joseph C. Gil; Aron Preis

(57) ABSTRACT

A UV-stabilizer comprising a mixture of hydroxybenzotriazole and a hydrolyzable silane containing at least one epoxy group is disclosed. The stabilizer is especially suitable as a component of a Siloxane system for coating substrates, especially thermoplastic substrates and most especially polycarbonate substrates.

12 Claims, No Drawings

UV-STABILIZERS FOR SILOXANE SYSTEMS

The present invention relates to non-volatile UV-stabilising mixtures for siloxane lacquer systems which mixtures have certain hydroxybenzotriazoles as the UV-stabilising active structure and which are thus particularly suitable for the UV-stabilisation of thermoplastics, in particular of aromatic polycarbonates.

Materials are frequently protected from the harmful influences of the environment by providing them with a protective surface. Siloxane-based lacquers have proved particularly suitable for this purpose, inter alia providing the materials with a scratch-resistant surface.

These lacquers may contain so-called UV-stabilising substances in order to protect the lacquer itself and the underlying material, the substrate, from harmful UV radiation. Apart from providing long-term UV protection, one requirement placed upon these substances is, inter alia, that they are not volatile so that they remain homogeneously distributed within the lacquer layer and do not escape from the lacquer layer either during curing or during subsequent use. The UV-stabilising substances must furthermore not decompose rapidly, must be durably homogeneously miscible with the lacquers and the lacquer containing the UV-stabilising substances should be transparent.

U.S. Pat. Nos. 4,278,804 and 4,051,161 relate to UV-stabilising active substances and lacquers containing them. The substances disclosed therein, however, exhibit the disadvantage that they provide inadequate UV protection, they decompose too rapidly and/or the siloxane system containing the stabilisers has a yellow tinge.

U.S. Pat. No. 5,438,142 furthermore discloses the UV-stabilising active substance, 1-(3'-(benzotriazol-2"-yl)-4'-hydroxyphenyl)-1,1-bis(4-hydroxyphenyl)ethane. This active substance, however, exhibits the disadvantage that it is not durably miscible with siloxane-based lacquers.

The object thus arises of providing a UV-stabiliser system which does not exhibit the above-stated disadvantages.

This object is achieved according to the invention by the provision of UV-stabilising mixtures containing hydroxybenzotriazole of the general formula (1) below and hydrolysable silanes containing epoxy groups.

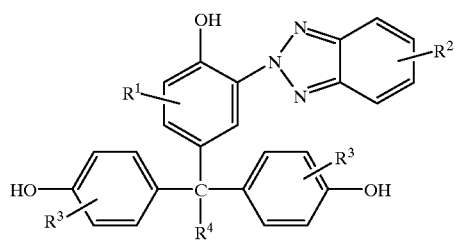

(1)

$R^1$: H, $C_1$–$C_{18}$ alkyl, $C_5$–$C_6$ cycloalkyl or $C_6$–$C_{12}$ aryl,
$R^2$: H, halogen, preferably Cl, or $C_1$–$C_{12}$ alkyl,
$R^3$: H, $C_1$–$C_{12}$ alkyl, halogen, preferably Cl or Br, or $C_6$–$C_{12}$ aryl,
$R^4$: H, $C_1$–$C_{18}$ alkyl or $C_6$–$C_{18}$ aryl.

The present invention furthermore provides UV-stabilising mixtures having a molar ratio of epoxy groups of the silane to the hydroxybenzotriazole of the general formula (1) which is greater than 2.5. preferably greater than 4, particularly preferably greater than 16. The molar ratio of epoxy units of the silane to the hydroxybenzotriazole of the general formula (1) should not, however, exceed 1:200.

The mixtures according to the invention are suitable for the UV-stabilisation of siloxane systems, in particular of scratch- and abrasion-resistant siloxane coating materials. Such UV-stabilised coating materials, preferably lacquers, may be used for coating materials of all kinds, such as for example wood, textiles, paper, stone articles, but preferably for coating plastics, metals, glass and ceramics, particularly preferably for coating thermoplastics and very particularly preferably for coating polycarbonates.

The hydroxybenzotriazoles used for the non-volatile, UV-stabilising mixtures according to the invention are compounds of the general formula (1).

Preferably, however, 1-(3'-(benzotriazol-2"-yl)-4'-hydroxyphenyl)-1,1-bis(4-hydroxyphenyl)ethane (hereinafter abbreviated to THPE-BZT) is used. The production of THPE-BZT is described in detail in U.S. Pat. No. 5,438,142, wherein the general synthetic pathway is disclosed in scheme 1 of said patent. The product is commercially obtainable from the company Hoechst/Celanese.

Silanes containing epoxy groups are generally taken to mean compounds which, on the one hand, possess at least one epoxy ring and simultaneously have groups which form silanol structures under hydrolysing conditions.

Epoxysilanes as are preferably used according to the invention are described, for example, in U.S. Pat. No. 9,946,701. They are compounds of the general formulae (2) or (3):

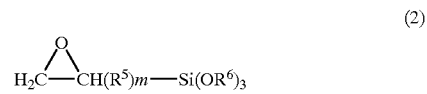

(2)

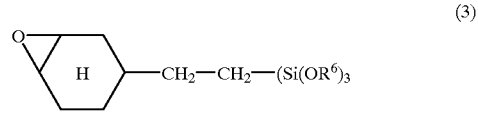

(3)

$R^5$ is a divalent hydrocarbon residue at most 9 carbon atoms or a divalent residue having at most 9 carbon atoms consisting of C, H and O atoms, wherein the O atom is present as an ether bond residue.

m is 0 or 1.

Production of these epoxysilanes is also described in U.S. Pat. No. 2,946,701. Reference is accordingly made to said patent. Particularly preferred epoxysilanes are those compounds in which $R_6$ is methyl or ethyl. They are commercially available, inter alia from the companies Union Carbide and Hüls AG as:

| | |
|---|---|
| A-187 or Dynasilan Glymo | 3-glycidyloxypropyltrimethoxysilane |
| A-186 | 2-(3,4-epoxycyclohexyl)ethyltrimethoxysilane. |

Production of the UV-stabilising Mixtures

The UV-stabilising mixtures are produced by homogeneously mixing hydroxy-benzotriazole of the general formula 1 with the hydrolysable silanes containing epoxy groups and heating this mixture. Heating should be performed for at least 30 minutes at at least 90° C. The temperature should preferably be above 120° C. during heating.

It has proved particularly favourable to use a mixing ratio at which stoichiometrically more epoxy groups are present than the two free phenolic OH groups not required for UV-stabilisation of the hydroxybenzotriazoles of the general formula (1). The molar ratio of epoxy units of the silane to hydroxybenzotriazole of the general formula 1 should thus be greater than 2.5, preferably greater than 4, particularly preferably greater than 16.

The UV-stabilising components need not necessarily be produced separately so that they may subsequently be added to the siloxane system to be stabilised, but may also be synthesised in situ as a sub-stage during synthesis of the siloxane systems/siloxane coating materials.

Siloxane Systems/Siloxane Coating Materials

The siloxane systems are substantially thermally curing systems which preferably crosslink by a condensation reaction to yield —Si—O—Si— linkages. Other crosslinking mechanisms may proceed in parallel. Such systems are described, for example, in U.S. Pat. Nos. 3,790,527, 3,865,755, 3,887,514, 4,243,720, 4,278,804, 4,680,232, 4,006,271, 4,476,281, in DE-A 4 011 045, 4 122 743, 4 020 316, 3 917 535, 3 706 714, 3 407 087, 3 836 815, 2 914 427, 3 135 241, 3 134 777, 3 100 532, 3 151 350, in DE-A 3 005 541, 3 014 411, 2 834 606, 2 947 879, 3 016 021, 2 914 427 and 4 338 361 and should be considered part of the present disclosure.

The present invention also provides siloxane systems UV-stabilised according to the invention.

Preferably used siloxane systems are those containing particulate material selected from among oxides, oxide hydrates, nitrides and carbides of Si, Al, Sb and B and of transition metals, preferably Ti, Ce, Fe and Zr, and having a particle size in the range from 1 to 100 nm, preferably from 2 to 50 nm.

The UV-stabilising mixture according to the invention should be added to the siloxane system in such a quantity, relative to the solids content of the siloxane system, that the proportion of hydroxybenzotriazole, relative to the solids content of the siloxane system, is 0.3 to 20, preferably 3 to 15, particularly preferably 5 to 10 wt. %.

Reference is made to DE-A 2 914 427 and DE-A 4 338 361 with regard to production of siloxane-based scratch-resistant coating systems and components thereof and these documents are thus part of the present description.

Substrates, Materials

The siloxane systems provided with the UV-stabilising mixture according to the invention may be used as bulk materials and as coating materials. There are no restrictions as to the substrate materials which may be selected for coating. These UV-stabilised coating materials are preferably suitable for coating wood, textiles, paper, stone articles, metals, glass, ceramics and plastics and in particular for coating thermoplastics, as are described in Becker/Braun Kunststoffhandbuch, Carl Hanser Verlag, Munich, Vienna, 1992. They are very particularly suitable for coating transparent thermoplastics, preferably polycarbonates.

Conventional coating processes are used for coating purposes, for example dipping, flooding, pouring, spinning, spraying or brushing.

The coating is applied to film thicknesses of, for example, 2 to 200 μm, preferably of 2 to 30 μm and particularly preferably of 5 to 15 μm. The substrate may optionally be primed with a coupling agent or primer coat before application of the coating.

The lacquers are preferably cured at temperatures of >90° C.

For the purposes of the present invention, thermoplastic, aromatic polycarbonates include both homopolycarbonates and copolycarbonates; the polycarbonates may, in a known manner, be linear or branched.

A proportion, up to 80 mol %, preferably of 20 mol % to 50 mol %, of the carbonate groups in the suitable polycarbonates may be replaced by aromatic dicarboxylic acid ester groups. Such polycarbonates, which contain both acid residues of carbonic acid and acid residues of aromatic dicarboxylic acids incorporated in the molecular chain, are more accurately termed polyester carbonates. They are to be subsumed within the superordinate term of thermoplastic, aromatic polycarbonates.

Details of the production of polycarbonates have been described in hundreds of patents over the past approx. 40 years. Reference is made, merely by way of example, to "Schnell, Chemistry & Physics of Polycarbonates", *Polymer Reviews*, volume 9, Interscience Publishers, New York, London, Sydney 1964, to D. C. Prevorsek, B. T. Debona & Y. Kesten, Corporate Research Center, Allied Chemical Corporation, Morristown, N.J. 07960, "Synthesis of poly (ester carbonate) copolymers" in *Journal of Polymer Science, Polymer Chemistry edition*, volume 19, 75–90 (1980), to D. Freitag, U. Grigo, P. R. Müller, N. Nouvertne', Bayer A G, "Polycarbonates" in *Encyclopedia of Polymer Science & Engineering*, volume 11, second edition, 1988, pages 648–718 and finally to Dr. U. Grigo, Dr. K. Kircher & Dr. P. R. Müller "Polycarbonate" in Becker/Braun, *Kunststoff-Handbuch*, volume 3/1, *Polycarbonate, Polyacetale, Polyester, Celluloseester*, Carl Hanser Verlag, Munich, Vienna, 1992, pages 117–299.

The thermoplastic polycarbonates have average molecular weights $\overline{M}_w$ (determined by measuring relative viscosity at 25° C. in $CH_2Cl_2$ and a concentration of 0.5 g per 100 ml of $CH_2Cl_2$) of 12000 to 400000, preferably of 18000 to 80000 and in particular of 22000 to 60000.

The present invention accordingly also provides coated materials, preferably polycarbonate and particularly preferably polycarbonate provided with a scratch-resistant coating.

EXAMPLES

Example 1 a) UV-stabilising Mixture of THPE-BZT and 3-glycidyloxypropyltrimethoxysilane (Glymo)

50 g of THPE-BZT and 450 g of 3-glycidyloxypropyltrimethoxysilane are introduced into a vessel and heated to 140 to 150° C. under a nitrogen atmosphere while being stirred and are maintained at this temperature for one hour.

This mixture (mixture 1) was varied as follows:

| Mixture: | | | |
|---|---|---|---|
| 2 | 100 g THPE-BZT | 400 g | Glymo |
| 3 | 150 g THPE-BZT | 350 g | Glymo |
| 4 | 200 g THPE-BZT | 300 g | Glymo |
| 5 | 100 g THPE-BZT | 400 g | α-(3,4-epoxycyclohexyl)ethyl-trimethoxysilane | b) Production of the Siloxane Coating Material According to DE-OS 2 914 427 (Coating Sol I)

α) 19.8 g of glacial acetic acid, 210 g of distilled water and 227 g of isopropanol are added to 300 g of colloidal silica having an $SiO_2$ content of 30 wt. %. After thorough mixing, 900 g of methyltriethoxysilane are added and the mixture heated to 60° C. while being stirred. The mixture is left at this temperature for 4 hours and then a further 1200 g of isopropanol are added to the mixture. Once the product has cooled to room temperature, the slightly opaque solution is filtered.

β) 340 g of isopropanol, 190 g of tetraethoxysilane and 360 g of methyltriethoxysilane are introduced into a vessel fitted with a stirrer and reflux condenser. This mixture is combined with 180 g of 0.05 n hydrochloric acid and co-hydrolysed by refluxing for five hours. The mixture is cooled to room temperature after the reaction. A solution is obtained which is a partial hydrolysate of tetraethoxysilane (5.1%, calculated as $SiO_2$) and a partial hydrolysate of methyltriethoxysilane (12.6%, calculated as $CH_3SiO_{1.5}$).

Before use as a coating material, the two components α) and β) are mixed together in a 1:1 ratio and dissolved in a mixture prepared from 60 parts by weight of n-butanol, 40 parts by weight of acetic acid and 20 parts by weight of toluene.

c) Production of a Siloxane Coating Material According to DE-OS 4 338 361 (Coating Sol II)

A boehmite sol was produced by combining 12.82 g of acetic acid-stabilised (6.4 wt. % acetic acid) boehmite powder with 104.62 g of 0.1 n HCl. Subsequent ultrasonication (20 minutes) produced a transparent, colourless solution, 24.3 g of which were combined with a mixture prepared from 118.17 g of GPTS (3-glycidyloxypropyltrimethoxysilane) and 62.50 g of TEOS (tetraethyl orthosilicate). The reaction mixture was stirred for 2 hours at room temperature and then, while being cooled with ice, combined with 18.93 g of aluminium tributoxyethanolate. The resultant clear sol was stirred for 2 hours at room temperature and then, while being cooled with ice, combined with 93.14 g of the above boehmite sol and 79.30 g of butoxyethanol.

d) UV-stabilised Coating Sols I and II

A 75 g portion of the UV-stabilising mixture 2 according to the invention was added to a 1000 g portion of each of coating sols I and II. Silica glass was coated with these compositions and UV light transmission measured with a Beckmann DU 70 photometer in the wavelength range from 250 to 600 nm. The coating film was 5 μm thick and absorbed >98% of the radiation of a wavelength of <350 nm critical for polycarbonate.

e) Coating of Substrates and Testing of Coating Properties

Bisphenol A polycarbonate sheets ($T_g$=147° C., $\overline{M}_w$ 27500) of dimensions 105×150×4 mm were cleaned with isopropanol and primed by dipping in a mixture prepared from 3 wt. % of aminopropyltrimethoxysilane and 97 wt. % of ethylene glycol monobutyl ether followed by 30 minutes' heat treatment at 130° C. The sheets were then provided with a 20 μm film of one of coating sols I or II at a dipping speed V=100 cm/min. After flashing off for 10 minutes at room temperature, the coated sheets were dried for 1 hour at 130° C. The film thickness of the scratch-resistant lacquers was approx. 5 μm after drying. Once curing was complete, the coated sheets were stored for 2 days at room temperature and then exposed to a defined quantity of UV radiation.

UV Exposure Testing

The polycarbonate sheets were exposed to filtered xenon arc radiation with a water spray cycle to DIN 53387-1-A-X under the following test conditions:

Weathering apparatus: Xenon-WOM
Radiation intensity at 340 nm: 0.35 W/m² (preferably)
Filter combination: inner: Pyrex, outer: Pyrex
Blackboard temperature: 60° C.±5° C.
Black standard temperature: 65° C.±3° C.
Mode of operation: constant
Water spray cycle: 102:18
Relative atmospheric humidity: 60–80%

Yellowing as a function of exposure time was used as the evaluation criterion for the weathering resistance of the lacquer-coated sheets. The corresponding yellowness of the sheets was determined as the Yellowness Index (Y.I.) to ASTM D 1925-70.

| Y.I. values after Xenon-WOM 102:18 weathering | | | | | |
|---|---|---|---|---|---|
| Specimens | 0 h | 1000 h | 2000 h | 3000 h | 5000 h |
| Polycarbonate with UV-stabilised coating sol I according to mixture 2 | 2.1 | 2.3 | 2.7 | 2.9 | 4.3 |
| Polycarbonate with UV-stabilised coating sol II according to mixture 2 | 2.4 | 2.6 | 3.1 | 3.2 | 4.9 |
| Comparison | | | | | |
| Polycarbonate according to Example 1e with coating sol II without UV stabilisation | 1.9 | 2.6 | 6.3[a] | 7.9[a] | —[b] |

[a]Cracks, delamination of lacquer film.
[b]No lacquer film remains.

What is claimed is:

1. A process for producing a UV stabilizer comprising mixing and heating to at least 90° C. for at least 30 minutes (A) a hydroxybenzotriazole conforming to

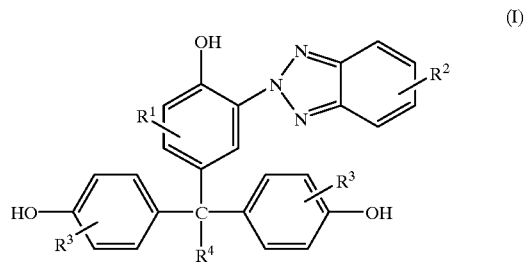

(I)

where
R¹ denoted a member selected from the group consisting of H, $C_{18}$-alkyl, $C_{5-6}$-cycloalkyl and $C_{6-12}$-aryl,
R² denotes a member selected from the group consisting of H, halogen and $C_{1-12}$-alkyl,
R³ denotes a member selected from the group consisting of H, $C_{1-12}$-alkyl, halogen and $C_{6-12}$-aryl and
R⁴ is a member selected from the group consisting of H, $C_{1-18}$-alkyl and $C_{6-18}$-aryl, and (B) at least one hydrolyzable silane containing at least one epoxy group.

2. The process of claim 1 wherein the molar ratio of said at least one epoxy group to said hydroxybenzotriazole is greater than 2.5.

3. The process of claim 1 wherein said (A) is 1-(3'-(benzotriazol-2''-yl)-4'-hydroxyphenyl)-1,1-bis(4-hydroxyphenyl)ethane.

4. A coated substrate prepared by the method of claim 1.

5. The UV-stabilizer produced in accordance with the process of claim 1.

6. A coating composition comprising siloxane and the UV-stabilizer of claim 5.

7. The coating composition of claim 6 wherein siloxane contains solids in the form of particulate material having a particle size in the range of 1 to 100 nm selected from a first group consisting of oxides, oxide hydrates, nitrides and carbides of at least one member selected from a second group consisting of Si, Al, Sb, B and a transition metal.

8. The coating composition of claim 7 wherein weight ratio of hydroxybenzotriazole to said solids is 0.3 to 20.

9. The coating composition of claim 8 wherein second group consists of Ti, Ce, Fe and Zr.

10. A method of using the UV-stabilizer of claim 5 comprising coating at least a part of the surface of a substrate therewith.

11. The method of claim 10 wherein substrate is thermoplastic.

12. The method of claim 11 wherein thermoplastic is polycarbonate.

* * * * *